(12) United States Patent
Kawarada

(10) Patent No.: US 7,851,205 B2
(45) Date of Patent: Dec. 14, 2010

(54) DNA SENSOR

(75) Inventor: Hiroshi Kawarada, Yokohama (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 692 days.

(21) Appl. No.: 11/661,033

(22) PCT Filed: Aug. 4, 2005

(86) PCT No.: PCT/JP2005/014283

§ 371 (c)(1),
(2), (4) Date: Jun. 1, 2007

(87) PCT Pub. No.: WO2006/025180

PCT Pub. Date: Mar. 9, 2006

(65) Prior Publication Data

US 2008/0032294 A1 Feb. 7, 2008

(30) Foreign Application Priority Data

Aug. 30, 2004 (JP) ............... 2004-250303

(51) Int. Cl.
*C12M 1/34* (2006.01)
*C12M 3/00* (2006.01)
*C12Q 1/68* (2006.01)
*H01L 27/148* (2006.01)
*G01N 27/403* (2006.01)
*C07H 21/04* (2006.01)

(52) U.S. Cl. ............ 435/287.2; 435/6; 257/243; 257/253; 536/24.3

(58) Field of Classification Search ........ 435/6, 435/287.2; 257/243, 253; 536/24.3
See application file for complete search history.

(56) References Cited

U.S. PATENT DOCUMENTS

2002/0157949 A1* 10/2002 Kawarada ............. 204/416
2003/0186262 A1* 10/2003 Cailloux ................. 435/6
2004/0121354 A1* 6/2004 Yazawa et al. ........... 435/6
2005/0123442 A1* 6/2005 Gu et al. ................. 422/57
2008/0286762 A1* 11/2008 Miyahara et al. ......... 435/6

FOREIGN PATENT DOCUMENTS

| JP | 2001 272372 | 10/2001 |
|----|-------------|---------|
| JP | 2002 286692 | 10/2002 |
| JP | 2003 90815 | 3/2003 |
| JP | 2004 109020 | 4/2004 |

OTHER PUBLICATIONS

Beaucage, Stratgies in the preparation of DNA oligonucleotide arrays for diagnostic applications, 2001, Current Medicinal Chemistry, 8, 1213-1244.*
Uslu et al, Label free fully electronic nucleic acid detection system based on field effect transistor device, 2004, Biosensors and Bioelectronics, 19, 1723-1731.*
Lu et al, invasive cleavage reactions on a DNA modified diamond surface,2004, Biopolymers, 73, 606-613.*
Hideo Hata, "DNA Attachment and Hybridization At the Diamond Surface", Dai 50 Kai Oyo Butsurigaku Kankei Rengo Koenkai Koen Yokoshu, vol. 2, p. 167, 2003.
Hiroshi Kawaharada, "Kinosei Diamond Hyomen Eno Seitai Bunshi Kotei Oyobi Biosensor Oyo" Waseda Daigaku Coe 'Bunshi Nano Kogaku' Kenkyu Kyoten, 'Nano Kozo Hairetsu O Kiban Tosuru Bunshi Nano Kogaku No Kochiku to Microfilm System Eno Tenkai' Jikken Hokokusho, pp. 161-162, 2004.

* cited by examiner

*Primary Examiner*—Robert T Crow
*Assistant Examiner*—Narayan K Bhat
(74) *Attorney, Agent, or Firm*—Oblon, Spivak, McClelland, Maier & Neustadt, L.L.P.

(57) ABSTRACT

A DNA sensor including a p-channel field-effect transistor having as a gate an electrolyte solution and having as a channel a diamond surface which contains a mixture of at least a hydrogen-terminated surface and a surface terminated by an amino group or a molecule with an amino group as an amino termination; a probe DNA constituted of a single-stranded DNA with known nucleotide sequence which is directly immobilized by a linker to the amino termination of the diamond surface; and a target DNA constituted of an unknown single-stranded DNA which is dropped on said diamond surface, wherein the hybridization of the target and probe is ascertained by detecting a shift of the threshold voltage of said p-channel field effect transistor toward positive direction which is due to increase in hole density of the p-channel resulting from doubling the negative electric charge of the phosphate groups upon hybridization.

15 Claims, 5 Drawing Sheets

DNA SENSOR

TECHNICAL FIELD

The present invention relates to a biosensor, and more particularly relates to a DNA (Deoxyribonucleic Acid) sensor (DNA chip) having a p-channel field effect transistor and a measuring method using the DNA sensor.

BACKGROUND ART

Conventional technologies in this field are those described in the following.

(1) Fluorescence Detection Method

This fluorescence detection method is to immobilize a single-stranded DNA with known nucleotide sequence (probe DNA) on a glass substrate, silicon, diamond, or the like and to detect the hybridization (a phenomenon in which mutually complementary single-stranded DNAs are coupled to form a double-stranded DNA) with unknown single-stranded DNA (target DNA) by a fluorescent substance immobilized on the target DNA. A problem lies here, however, in large scale apparatus necessary to detect the hybridization by means of fluorescence in this method. Furthermore, a limitation is also present in realization in high density because the observation means is a fluorescence microscope.

(2) Electric Charge Detection Method

This electric charge detection method is based on a silicon ISFET (Ion Sensitive Field Effect Transistor). The sensitivity of the silicon ISFET is, however, too low to detect the doubling of the charge due to the hybridization of DNA.

(3) High Performance p-Channel Field Effect Transistor with enhanced threshold voltage resulting from ozone treatment, as Suggested by Present Inventors This transistor is a p-channel field effect transistor having an electrolyte solution gate and having as a channel a diamond surface which is a mixture of a hydrogen terminated surface and an oxygen terminated surface produced by oxidization of the hydrogen terminated surface by an ozone treatment (see patent document 1 below).

[Patent document 1]

Japanese Unexamined Patent Publication No. 2004-109020

DISCLOSURE OF INVENTION

The present invention is a further improvement of the charge detection method (2) (charge detection type DNA chip) described above, and aims at providing a DNA sensor and a measuring method using the DNA sensor capable of identifying an unknown DNA by increasing detection sensitivity of the hybridization by means of directly immobilizing a DNA on the diamond surface of a p-channel field effect transistor having an electrolyte solution gate and having as a channel a diamond surface which is a mixture of a hydrogen terminated surface and a surface terminated by an amino group or a molecule with an amino group as an amino termination.

To achieve the above objects, the present invention provides the following:

[1] A DNA sensor including a p-channel field-effect transistor having an electrolyte solution gate and having as a channel a diamond surface which contains a mixture of at least a hydrogen-terminated surface and a surface terminated by an amino group or a molecule with an amino group as an amino termination; a probe DNA constituted of a single-stranded DNA with known nucleotide sequence which is directly immobilized by a linker to the amino termination of the diamond surface; and a target DNA constituted of an unknown single-stranded DNA which is dropped on the diamond surface. When the target DNA is in complementary relationship to the probe DNA, due to a double-stranded DNA produced by the hybridization of the probe DNA with the target DNA both constituted of the single-stranded DNA, the threshold voltage of the p-channel field effect transistor shifts toward positive direction. The DNA sensor according to the present invention is characterized by that an identification on whether or not the target DNA is in complementary relationship to the probe DNA is performed by detecting the shift of this threshold voltage toward positive direction.

[2] In the DNA sensor according to the above item [1], the diamond surface contains an oxygen-terminated surface.

[3] In the DNA sensor according to one of the above items [1] and [2], the linker is divalent or trivalent carboxylic acid.

[4] In the DNA sensor according to one of the above items [1] and [2], the linker is divalent or trivalent aldehyde.

[5] In the DNA sensor according to one of the above items [1], [2], [3] and [4], the density of the probe DNA is equal to or greater than $10^{10}$ cm$^{-2}$, and the density of the target DNA is from $10^{-12}$M to $10^{-6}$M.

[6] In the DNA sensor according to one of the above items [1], [2], [3] and [4], the shifting difference of the threshold voltage toward positive direction is detected as a change in the gate voltage under a constant drain current.

[7] In the DNA sensor according to one of the above items [1], [2], [3] and [4], the shifting difference of the threshold voltage toward positive direction is detected as a change in the drain current under a constant gate voltage.

[8] In the DNA sensor according to one of the above items [1], [2], [3] and [4], the shifting difference of the threshold voltage toward positive direction is detected as a change in the drain current under a constant drain voltage.

[9] A measuring method using a DNA sensor including setting a p-channel field-effect transistor having as a gate an electrolyte solution and having as a channel a diamond surface which contains a mixture of at least a hydrogen-terminated surface and a surface terminated by an amino group or a molecule with an amino group as an amino termination; a probe DNA constituted of a single-stranded DNA with known nucleotide sequence which is directly immobilized by a linker to the amino termination of said diamond surface; and a target DNA constituted of an unknown single-stranded DNA which is dropped on said diamond surface, wherein an identification on whether or not said target DNA is in complementary relationship to said probe DNA is performed by detecting a shift of the threshold voltage of said p-channel field effect transistor toward positive direction, the shift resulting from a double-stranded DNA produced by hybridization of said probe DNA with said target DNA both constituted of the single-stranded DNA, the hybridization which occurs when said target DNA is in complementary relationship to said probe DNA.

BEST MODE FOR CARRYING OUT THE INVENTION

For a DNA sensor, a p-channel field-effect transistor having an electrolyte solution as a gate and having a diamond surface as a channel (SGFET: Electrolyte Solution Gate Diamond Field Effect Transistor), the diamond surface containing a mixture of at least a hydrogen-terminated surface and a surface terminated by an amino group or a molecule with an amino group as an amino termination, is configured along with a probe DNA constituted of a single-stranded DNA with known nucleotide sequence which is directly immobilized by a linker to the amino termination of the diamond surface and with a target DNA, constituted of an unknown single-stranded DNA on the diamond surface. When the target DNA is in complementary relationship to the probe DNA, the (negative) electric charge of the phosphate group of a double-stranded DNA produced by the hybridization of the probe DNA with the target DNA both constituted of a single-stranded DNA is doubled, thereby resulting in increase of the hole density in the p-channel and shift of the threshold voltage of the p-channel field effect transistor toward positive direction. The DNA sensor according to the present invention is characterized by detection of the shift of this threshold voltage toward positive direction to identify whether or not the target DNA is in complementary relationship to the probe DNA. Hence, a prompt and accurate identification of DNA is made possible.

Preferred embodiments of the invention will be described in more detail in the following.

DNA has a negative electric charge due to the phosphate group, and the negative charge is approximately doubled by performing hybridization. The present invention enables identification of DNA by detecting an extent of increase in hole number in the channel resulting from immobilizing the DNA with significant change in the amount of the negative charge onto the diamond channel surface of the SGFET.

The DNA sensor in accordance with the present invention is described in the following.

Figure 1:
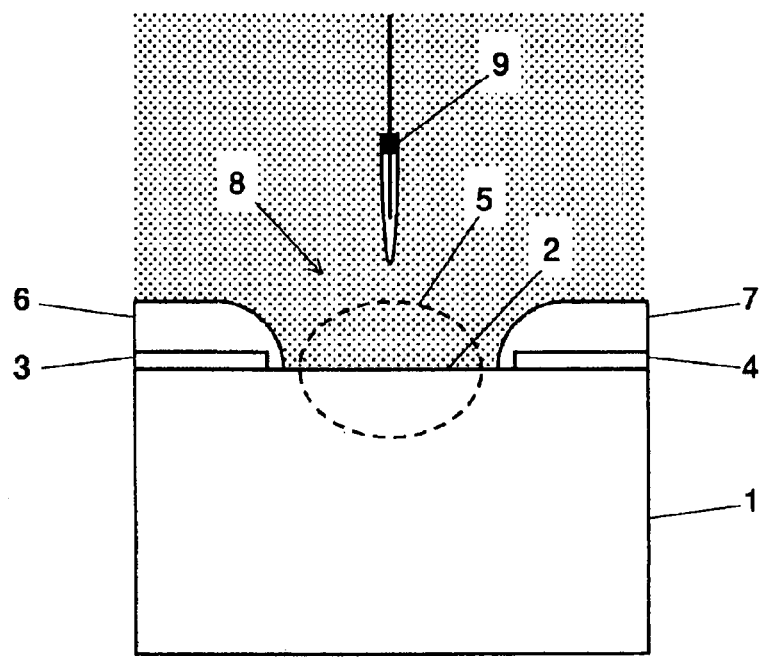
FIG. 1 illustrates a cross sectional view of an electrolyte solution gate field effect transistor (SGFET) according to the present invention.
Figure 2:
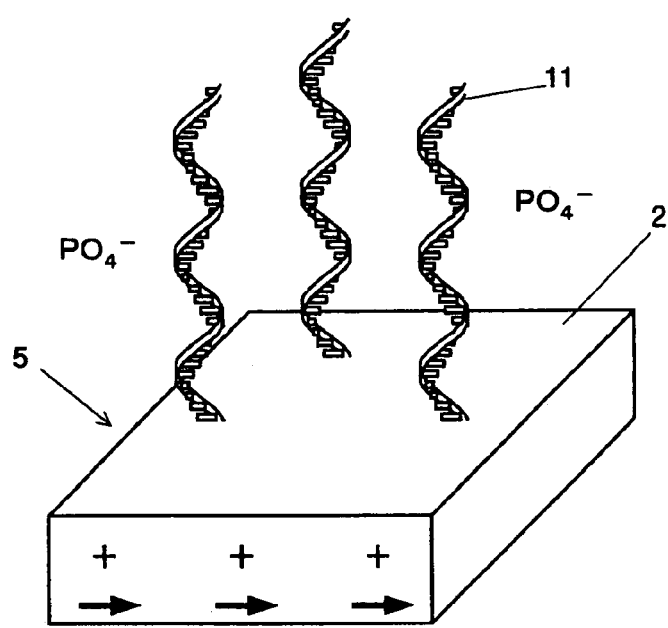
FIG. 2 is a schematic diagram of a channel showing generation of negative electric charge due to single-stranded DNA in accordance with an embodiment of the present invention.
Figure 3:
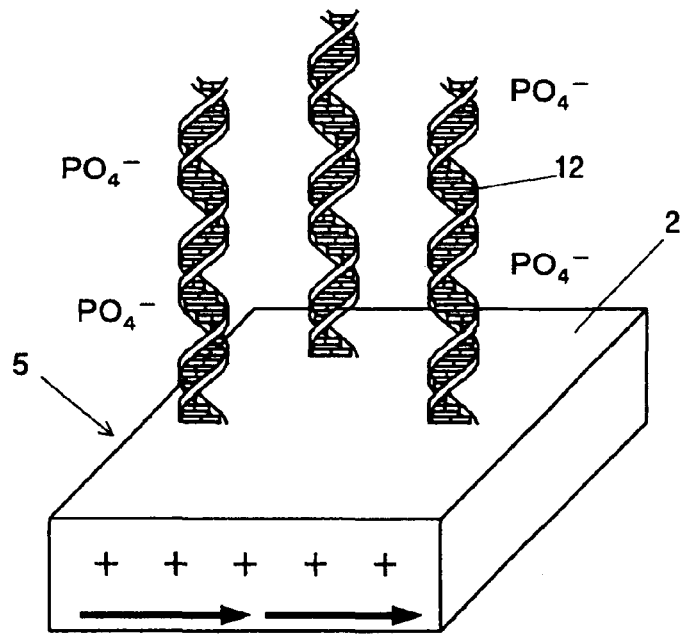
FIG. 3 is a schematic diagram of a channel showing generation of negative electric charge due to double-stranded DNA in accordance with an embodiment of the present invention.
Figure 4:
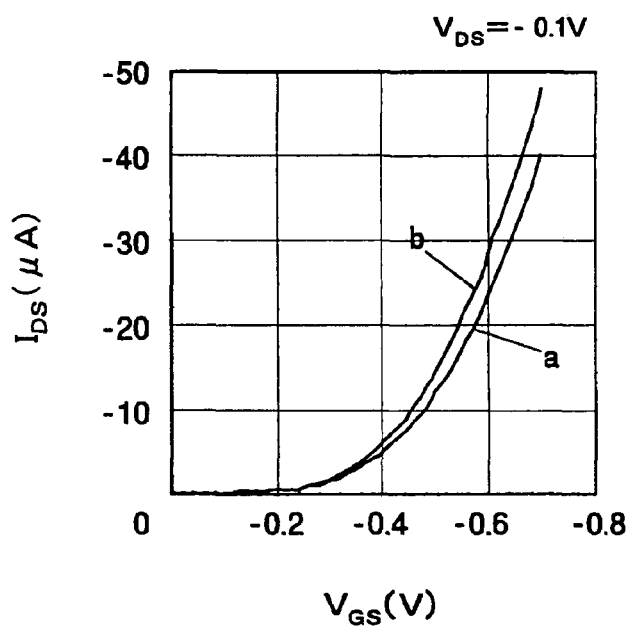
FIG. 4 is a diagram showing a change of the SGFET characteristics (No. 1) in accordance with an embodiment of the present invention.
Figure 5:
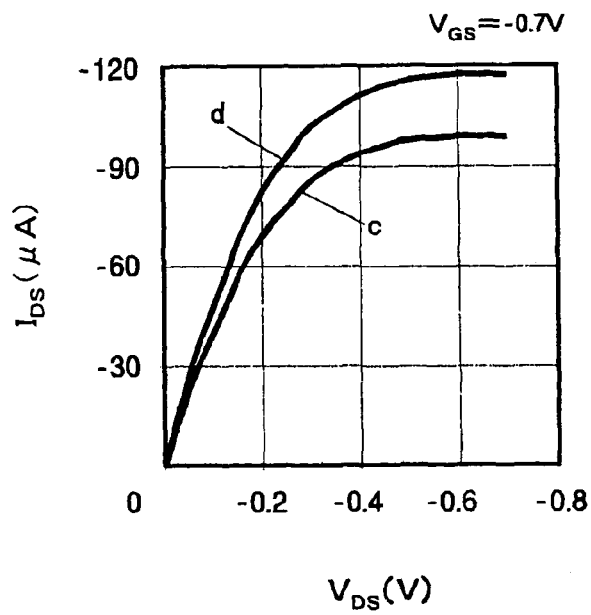
FIG. 5 is a diagram showing a change of the SGFET characteristics (No. 2) in accordance with an embodiment of the present invention.

FIG. 1 illustrates a cross sectional view of a SGFET according to the present invention. FIG. 2 is a schematic diagram of a channel showing generation of negative electric charge due to a single-stranded DNA in accordance with an embodiment of the present invention. FIG. 3 is a schematic diagram of a channel showing generation of negative electric charge due to a double-stranded DNA in accordance with an embodiment of the present invention. FIG. 4 is a diagram showing a change of the SGFET characteristics (No. 1). FIG. 5 is a diagram showing a change of the SGFET characteristics (No. 2).

(1) As shown in FIG. 1, a p-channel 5 made of a diamond surface 2 is formed sandwiched between a source electrode 3 and a drain electrode 4 on the diamond surface 2 of an undoped polycrystalline diamond layer 1. The diamond surface 2 contains a mixture of a hydrogen terminated and an amino terminated surfaces, and insulating layers 6 and 7 of polyimide resin are formed on the source electrode 3 and the drain electrode 4, respectively. On the p-channel 5, a gate 8 is formed of an electrolyte solution. Reference numeral 9 represents a reference electrode disposed in the electrolyte solution 8. In addition, a substrate is not limited to the polycrystalline diamond layer, but a single crystal diamond layer or nano crystalline diamond may be used alternatively.

In this way, a p-channel field-effect transistor having an electrolyte solution as a gate 8 and having as a p-channel 5 a diamond surface 2 which contains a mixture of a hydrogen-terminated and an amino-terminated surfaces is prepared.

(2) Next, as shown in FIG. 2, a probe DNA 11 constituted of a single stranded DNA with known nucleotide sequence is directly immobilized covalently onto the amino termination on the p-channel 5 of the diamond surface 2 by bridge reaction through a linker (for example, divalent or trivalent carboxylic acid (succinic acid, phthalic acid) or divalent or trivalent aldehyde (glutaraldehyde)). In this case the probe DNA 11 is immobilized at a density as high as equal to or greater than $10^{10}$ cm$^{-2}$.

In addition, an amino termination in the embodiment refers not only to the case where an amino group is stuck directly on the diamond surface 2 but also to the case where an amino group is stuck on an end of a molecule immobilized on the diamond surface. In this sense, description can be changed to a surface terminated by an amino group or a molecule containing an amino group.

Furthermore, as the linker, an acid or an acid compound is used for example, and divalent or trivalent carboxylic acid (COOH group) and divalent or trivalent aldehyde (COH group) are preferable.

(3) Next, a target DNA with unknown nucleotide sequence (concentration from $10^{-12}$ M to $10^{-6}$ M) is dropped onto the p-channel 5 to which the probe DNA 11 is immobilized. Here, in the case where the probe DNA 11 and the dropped target DNA are in the complementary relationship, the hybridization occurs which changes the probe DNA 11 to a double-stranded DNA 12 as shown in FIG. 3. In this case, the amount of the phosphate group doubles and therefore, its negative electric charge also doubles, thereby increasing the hole density in the p-channel and shifting the threshold voltage of SGFET toward positive direction.

Then, this threshold voltage difference of SGFET can be detected either as a change (a shift toward positive direction) of gate voltage $V_{GS}$ (a voltage between the gate and the source) under a constant drain current $I_{DS}$ (a current between the drain and the source) condition (in reference to the horizontal axis of FIG. 4) as shown in FIG. 4, or as a change of the drain current $I_{DS}$ (an increase in the absolute value) under a constant gate voltage $V_{GS}$ condition (in reference to the vertical axis of FIG. 4), or as a change of the drain current $I_{DS}$ (an increase in the absolute value) under a constant drain voltage $V_{DS}$ (a voltage between the drain and the source) condition (in reference to the vertical axis of FIG. 5) as shown in FIG. 5.

FIG. 4 shows the characteristic diagram (No. 1) of the SGFET (Here $Vp_s$ (V) [drain voltage] is set at −0.1V). In this diagram, curve a shows $I_{DS}$ (μA) [drain current] vs. $V_{GS}$ (V) [gate voltage] characteristics of the SGFET in the case where only the probe DNA 11 constituted of single-stranded DNA is immobilized on the diamond surface 2, and curve b shows $I_{DS}$ (μA) [drain current] vs. $V_{is}$ (V) [gate voltage] characteristics of the SGFET in the case where a double-stranded DNA 12 is formed by hybridization. In this case the concentration of the target DNA (21 base pairs) is 0.1 nM, and pH of the bulk solution is equal to 7.

FIG. 5 shows the characteristic diagram (No. 2) of the SGFET (Here $V_{GS}$ (V) [gate voltage] is set at −0.7V). In this diagram, curve c shows $I_{DS}$ (μA) [drain current] vs. $Vp_s$ (V) [drain voltage] characteristics of the SGFET in the case where only the probe DNA 11 constituted of single-stranded DNA is immobilized on the diamond surface 2, and curve d shows $I_{DS}$ (μA) [drain current] vs. $V_{DS}$ (V)[drain voltage] characteristics of the SGFET in the case where a double-stranded DNA 12 is formed by hybridization. In this case, the concentration of the target DNA (21 base pairs) is 0.1 nM, and pH of the bulk solution is equal to 7.

As clearly understood from these figures, when looking at the change of gate voltage $V_{is}$ under a constant drain current $I_{DS}$, curve b shifts toward positive direction as compared with curve a. Similarly, when looking at the change of drain current $I_{DS}$ under a constant gate voltage $V_{is}$, curve b shifts toward negative direction as compared with curve a.

In this way, by detecting the existence of the shift toward positive direction of the threshold voltage of the p-channel field effect transistor, an identification can be made on whether the hybridization is present or not, in other word, the unknown DNA is in complementary relationship with the probe DNA or not.

In addition, in a case where the unknown target DNA is not in complementary relationship with the probe DNA 11, the hybridization scarcely happens, so that the shift toward positive direction of the threshold voltage of the SGFET does not occur, or even if it occurs it is small as compared to the complementary case.

Figure 6:
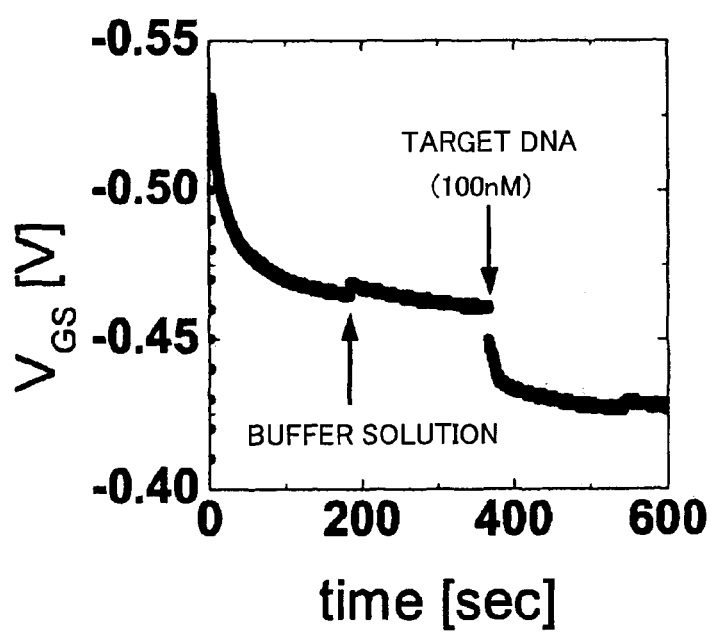
FIG. 6 is a diagram showing a temporal change of the SGFET gate voltage due to the DNA hybridization in accordance with an embodiment of the present invention.

FIG. 6 is a diagram showing a temporal change of the SGFET gate voltage due to the DNA hybridization in accordance with an embodiment of the present invention. Here, $V_{DS}$ (V) [drain voltage] is −0.4V, and $I_{DS}$ (μA) [drain current] is −10 μA.

From this figure, the gate voltage of the diamond surface can be confirmed to shift toward positive direction when a target DNA complementary to the probe DNA is dropped onto the probe DNA. This is considered due to increase in hole density in the channel resulting from doubling in amount of the phosphate group having negative electric charge by the hybridization. No change in the threshold voltage is observed for a target DNA not in complementary relationship. This method is a realtime, label-free detection method for the hybridization which is difficult by the conventional DNA chip. Along with biocompatibility of the diamond, the present sensor is expected as a sensor for practical usage in wide range of clinical application.

Figure 7:
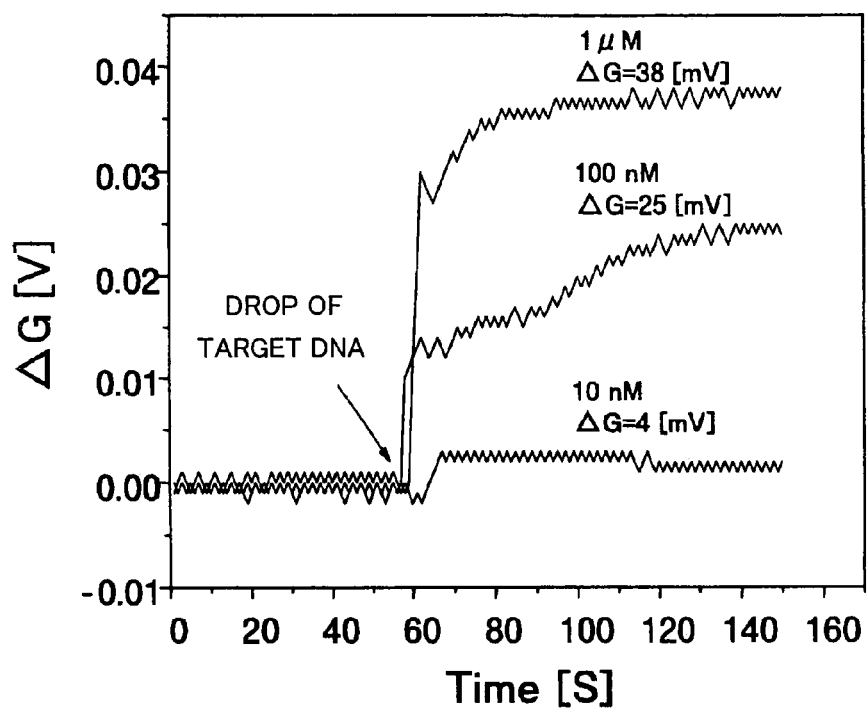
FIG. 7 is a diagram showing threshold voltage (gate voltage) characteristics in a case of changing the quantity of the target DNA in accordance with an embodiment of the present invention.

FIG. 7 is a diagram showing threshold voltage (gate voltage) characteristics in a case of changing the quantity of the target DNA in accordance with an embodiment of the present invention.

FIG. 7 shows temporal changes of the gate voltage under a constant drain current condition after a target DNA constituted of a single-stranded DNA in complementary relationship with the probe DNA is dropped at a time of 60 s. ΔG(V) on the vertical axis represents the amount of the gate voltage shift to positive direction due to the hybridization. In the case where the quantity of the dropped target DNA is 1 μM, 100 nM, and 10 nM, the positive shift is 38 mV, 25 mV, and 4 mV, respectively.

In the following, a specified embodiment will be described.

A p-channel field-effect transistor (SGFET) having an electrolyte solution (buffer solution) as a gate and having as a channel a polycrystalline or single crystalline diamond surface which contains a mixture of a hydrogen-terminated surface and an amino-terminated surface was prepared. A probe DNA with known nucleotide sequence and with a concentration of equal to or greater than $10^{10}$ cm$^{-2}$ was directly immmobilized through glutaraldehyde (divalent aldehyde) to the diamond surface by bridge bonding. Target DNAs each complementary and not complementary to this probe DNA with a concentration between $10^{-12}$M to $10^{-6}$M were dropped on the above described SGFET to which the probe DNA was immobilized. Under a constant drain current condition, real time measurement of the gate voltage change due to the hybridization was performed. As a result, positive direction shift of the gate voltage by 4 mV, 25 mV and 38 mV could be observed at the target DNA concentration of 10 nM, 100 nM, and 1 μM, respectively. No shift was detected for the target DNA not in complementary relationship.

As described above, the DNA sensor in accordance with the present invention is suitable for real time detection of DNA, and along with biocompatibility of the diamond channel surface, it is expected as a device for practical usage in the clinical application.

Figure 8:
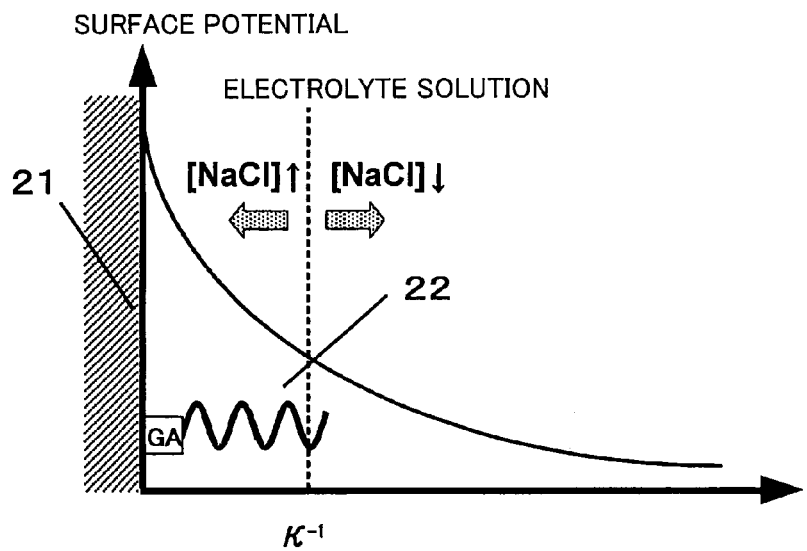
FIG. 8 is a diagram showing Debye length used in an experiment for optimization of the concentration of the buffer solution in accordance with an embodiment of the present invention.

Next, optimization in the concentration of buffer (NaCl) solution was examined experimentally. FIG. 8 is a diagram showing Debye length (Debye screening length) used in an experiment for optimization of the concentration of the buffer solution in accordance with an embodiment of the present invention. The horizontal axis shows a distance from the diamond surface, and the vertical axis represents the surface potential of the diamond.

Hybridization efficiency and detection efficiency for negative electric charge of the phosphate group (DNA) are in an antinomy (trade-off) relationship. In other words, higher concentration of buffer (NaCl) solution enables more screening of repulsion between negative electric charges, resulting in increase of the hybridization efficiency. On the other hand, detection efficiency for negative electric charge of the phosphate group (DNA) is higher for lower concentration of the buffer solution and longer Debye length.

In FIG. 8, reference numeral 21 denotes a diamond surface, reference numeral 22 denotes DNA (~20 nucleotides: ~6 nm), buffer solution is NaCl solution, and Debye length $\kappa^{-1}$ (nm) is given by $$\kappa^{-1}(nm) = 0.304/\sqrt{(NaCl)}$$

Here, ion species in the buffer solution is NaCl, and detectable length of DNA depending on NaCl concentration is shown in Table 1.

[Table 1]

TABLE 1

| | Buffer Solution | [NaCl] (M) | Debye Length (nm) |
|---|---|---|---|
| (1) | 20xssc | 3 | 0.18 |
| (2) | 2xssc | 0.3 | 0.56 |

TABLE 1-continued

| | Buffer Solution | [NaCl] (M) | Debye Length (nm) |
|---|---|---|---|
| (3) | 1xssc | 0.15 | 0.78 |
| (4) | 10 mM PBS | 0.01 | 3.04 |

(1) In a case of the buffer solution of 20 ssc, NaCl concentration is 3M, and Debye length is 0.18 nm, (2) in a case of the buffer solution of 2 ssc [1/10 of the buffer solution (1) above], NaCl concentration is 0.3M, and Debye length is 0.56 nm, (3) in a case of the buffer solution of 1 ssc [1/20 of the buffer solution (1) above], NaCl concentration is 0.15M, and Debye length is 0.78 nm, and (4) in a case of phosphate buffer solution (PBS) of 10 mM, NaCl concentration is 0.01M, and Debye length is 3.04 nm.

As clearly understood from the above description, in the case of the buffer solution of 2 ssc described above in (2), NaCl concentration is 0.3M and Debye length is 0.56 nm, which optimizes the hybridization of DNA, but Debye length is too short. In the case of the buffer solution given above in (3), Debye length becomes a little bit longer and the hybridization efficiency is still high, so that it is suitable for real time measurement. The buffer solution given above in (4) is used for measuring the static characteristics (FET characteristics).

Figure 9:
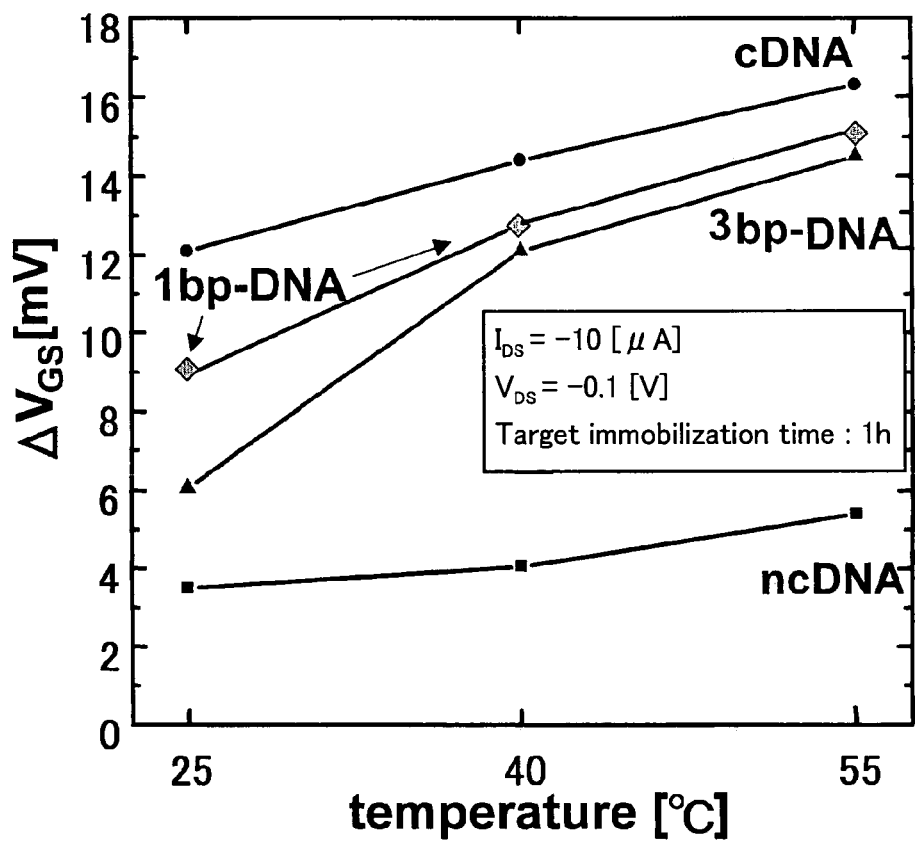
FIG. 9 is a diagram showing a change of the gate voltage shift by adjusting a temperature of the buffer solution in accordance with an embodiment of the present invention.

In addition, use was made here of short linker, glutaraldehyde (GA). A short linker is advantageous to accommodate more of the phosphate group of DNA within the Debye length. Furthermore, the hybridization is sensitive to the buffer solution temperature, and 59° C. is the optimum temperature. Nevertheless in this case, the buffer solution temperature was set at 40° C., and target DNAs with mismatched single and triple nucleotides are separately detected by reducing the hybridization efficiency. Additionally, by reducing the buffer solution temperature down to 25° C., triple nucleotide mismatch and single nucleotide mismatch were separated as shown in FIG. 9. Here, in FIG. 9, $I_{DS}$ (a current between the drain and the source) is −10 µA, $V_{DS}$ (a voltage between the drain and the source) is −0.1V, immobilizing time for target is 1 hour, the horizontal axis shows temperature [° C.], and the vertical axis is ΔV (shift voltage) [mV] between the gate and the source.

From the description above, a comparison is made in performance between the present invention and the conventional technology. Reducing the hybridization efficiency by lowering the setting temperature of the buffer solution from 59° C. which is the optimum temperature for the hybridization, to 40° C., and further to 25° C., wrong (imperfect) hybridization of target DNA with mismatched single and triple nucleotides was suppressed, and separate detection of single nucleotide and triple nucleotide mismatch was successfully performed. No report exists on such a high sensitivity measurement by using the conventional Si ISFET.

In addition, the present invention is expected to have a wide range of application as a mass consumption sensor not only in the medical field but also in food inspection, environmental measurement and the like, by reducing the device cost realized by mean of mass production. This invention is thus of great significance with economical and social influences.

The present invention is not limited to the above-described embodiment, various modifications can be made without departing from the scope of the invention, and these modifications shall not be excluded from the scope of the invention.

According to the present invention, the following advantages can be obtained.

(1) As a DNA sensor, detection sensitivity for the hybridization is increased, and an identification of unknown DNA can be performed.

(2) A prompt and accurate realtime detection for DNA can be performed.

In more detail, by the high sensitivity DNA immobilizing technology which is being made possible using diamond and by the size reduction in SGFET, the present invention can be expected for higher sensitivity detection than the conventional semiconductor biosensor or optical detection biosensor by using fluorescent label. Since reduction of specimen quantity necessary for measurement becomes possible by using the present DNA sensor, it can be used in the daily inspection and urgent inspection in the clinical inspection room. A device for detecting electric charge and electric potential suitable for integrated nanoscale device including other functions is also possible to realize.

In the above description, the diamond surface is referred to as a surface containing a mixture of a hydrogen-terminated surface and an amino-terminated surface. Additionally, an oxygen-terminated surface may be contained in the diamond surface as long as the occupancy rate of the oxygen-terminated surface is kept not to damage the function of the DNA sensor.

INDUSTRIAL APPLICABILITY

The DNA sensor in accordance with the present invention is suitable for realtime detection of DNA, and by making use of the biocompatibility of the diamond channel surface, this device can be utilized as a device for clinical application.

In addition, the present invention is expected to have a wide range of application as a mass consumption sensor not only in the medical field but also in food inspection, environmental measurement and the like, by reducing the device cost realized by mean of mass production. This invention is thus of great significance with economical and social influences.

Furthermore, due to the biocompatibility of carbon, the present device will have a potential application as a sensor embedded in living body.

The invention claimed is:

1. A DNA sensor comprising:
   (a) a p-channel field-effect transistor having as a gate an electrolyte solution and having as a channel a diamond surface which contains a mixture of at least (i) a hydrogen-terminated surface, and (ii) an oxygen terminated surface, and (iii) a surface terminated by an amino group;
   (b) a probe DNA constituted of a single-stranded DNA with known nucleotide sequence which is directly immobilized by a linker to the amino group of said diamond surface; and
   (c) a target DNA constituted of an unknown single-stranded DNA which is dropped on said diamond surface,
   (d) wherein an identification on whether or not said target DNA is in complementary relationship to said probe DNA is performed by detecting a shift of the threshold voltage of said p-channel field effect transistor toward positive direction, which is due to increase in hole density of the p-channel resulting from doubling the negative electric charge of the phosphate group of a double-stranded DNA produced by hybridization of said probe DNA with said target DNA both constituted of the single-stranded DNA, the hybridization which occurs when said target DNA is in complementary relationship to said probe DNA.

2. The DNA sensor according to claim 1 wherein said linker is divalent or trivalent carboxylic acid.

3. The DNA sensor according to claim 2 wherein the density of said probe DNA is equal to or greater than $10^{10}$ cm$^{-2}$, and the density of said target DNA is from $10^{-12}$M to $10^{-6}$M.

4. The DNA sensor according to claim 2 wherein said shifting difference of the threshold voltage toward positive direction is detected as a change in the gate voltage under a constant drain current.

5. The DNA sensor according to claim 2 wherein said shifting difference of the threshold voltage toward positive direction is detected as a change in the drain current under a constant gate voltage.

6. The DNA sensor according to claim 2 wherein said shifting difference of the threshold voltage toward positive direction is detected as a change in the drain current under a constant drain voltage.

7. The DNA sensor according to claim 1 wherein said linker is divalent or trivalent aldehyde.

8. The DNA sensor according to claim 7 wherein the density of said probe DNA is equal to or greater than $10^{10}$ cm$^{-2}$, and the density of said target DNA is from $10^{-12}$M to $10^{-6}$M.

9. The DNA sensor according to claim 7 wherein said shifting difference of the threshold voltage toward positive direction is detected as a change in the gate voltage under a constant drain current.

10. The DNA sensor according to claim 7 wherein said shifting difference of the threshold voltage toward positive direction is detected as a change in the drain current under a constant gate voltage.

11. The DNA sensor according to claim 7 herein said shifting difference of the threshold voltage toward positive direction is detected as a change in the drain current under a constant drain voltage.

12. The DNA sensor according to claim 1 wherein the density of said probe DNA is equal to or greater than $10^{10}$ cm$^{-2}$, and the density of said target DNA is from $10^{-12}$M to $10^{-6}$M.

13. The DNA sensor according to claim 1 wherein said shifting difference of the threshold voltage toward positive direction is detected as a change in the gate voltage under a constant drain current.

14. The DNA sensor according to claim 1 wherein said shifting difference of the threshold voltage toward positive direction is detected as a change in the drain current under a constant gate voltage.

15. The DNA sensor according to claim 1 wherein said shifting difference of the threshold voltage toward positive direction is detected as a change in the drain current under a constant drain voltage.

* * * * *